(12) United States Patent
Green

(10) Patent No.: US 9,637,419 B2
(45) Date of Patent: May 2, 2017

(54) METHOD OF PROCESSING ORGANIC WASTE

(71) Applicant: Lawrence R. Green, Lakewood, WA (US)

(72) Inventor: Lawrence R. Green, Lakewood, WA (US)

(*) Notice: Subject to any disclaimer, the term of this patent is extended or adjusted under 35 U.S.C. 154(b) by 0 days.

(21) Appl. No.: 15/183,296

(22) Filed: Jun. 15, 2016

(65) Prior Publication Data

US 2016/0297724 A1 Oct. 13, 2016

Related U.S. Application Data

(62) Division of application No. 14/003,937, filed as application No. PCT/US2012/028612 on Mar. 9, 2012, now Pat. No. 9,394,548.

(Continued)

(51) Int. Cl.
*C12P 1/00* (2006.01)
*C09K 17/16* (2006.01)
(Continued)

(52) U.S. Cl.
CPC .......... *C05F 17/0036* (2013.01); *C05B 17/00* (2013.01); *C05F 5/00* (2013.01); *C05F 9/04* (2013.01); *C05F 11/00* (2013.01); *C05F 17/009* (2013.01); *C05F 17/0018* (2013.01); *C05F 17/02* (2013.01); *C05G 3/04* (2013.01); *C09K 17/16* (2013.01); *C12P 1/00* (2013.01); *Y02P 20/145* (2015.11); *Y02W 30/43* (2015.05); *Y02W 30/47* (2015.05)

(58) Field of Classification Search
CPC ..... Y02W 30/47; Y02W 30/43; Y02P 20/145; C09K 17/16; C12P 1/00; C05F 17/02; C05F 17/009; C05F 5/00; C05F 11/08; C05F 11/00; C05F 17/0018
See application file for complete search history.

(56) References Cited

U.S. PATENT DOCUMENTS

| 5,571,703 | A | * | 11/1996 | Chieffalo | ................. B09B 3/00 426/11 |
| 2004/0000179 | A1 | * | 1/2004 | Hiraki | ................. C05F 17/0036 71/10 |

(Continued)

OTHER PUBLICATIONS

Kim, et al., Production of Weak Acid by Anaerobic Fermentation of Soil and Antifungal Effect, J. Microbiol. Biotechnol. (2007), 17(4), 691-694.*

(Continued)

*Primary Examiner* — William H Beisner
*Assistant Examiner* — Danielle Henkel
(74) *Attorney, Agent, or Firm* — George A. Leone; Citadel Patent Law

(57) ABSTRACT

Wheat bran culture mix is used to inoculate organic waste and produce an inoculated waste material, where the wheat bran culture mix includes soil derived microbes. The inoculated waste material is shredded to produce shredded inoculated waste material which is fermented the shredded inoculated waste material for at least 7 days. Contents from the fermenter are then transferred into a dewatering device to produce dewatered contents which are then separated into soluble and suspended products.

20 Claims, 7 Drawing Sheets

Related U.S. Application Data

(60) Provisional application No. 61/451,546, filed on Mar. 10, 2011.

(51) Int. Cl.
| | | |
|---|---|---|
| *C05F 5/00* | (2006.01) |
| *C05F 11/00* | (2006.01) |
| *C05F 17/00* | (2006.01) |
| *C05F 17/02* | (2006.01) |
| *C05B 17/00* | (2006.01) |
| *C05F 9/04* | (2006.01) |
| *C05G 3/04* | (2006.01) |

(56) References Cited

U.S. PATENT DOCUMENTS

2004/0182780 A1\* 9/2004 Lee ............... C02F 3/34
 210/610
2008/0105018 A1\* 5/2008 Grech ............ C05B 17/00
 71/7

OTHER PUBLICATIONS

The Compost-Gardener.com, Try Bokashi Composting—A Practical Solution for the Kitchen Compost, WayBackMachine Internet Archives, Copyright 2008-2009.\*

\* cited by examiner

| Attribute | Composting | Anaerobic Digestion | Bokashi Fermentation |
|---|---|---|---|
| Decomposition Time | ~ 6 months | ~ 30 days | ~20 days |
| Reduce Landfill biomass | yes | yes | yes |
| Requires Energy Tending | yes | yes | no |
| Contributes to global warming | yes | yes | no |
| Expensive to support and implement | yes | yes | no |
| Pathogen in Process Growth | yes | yes | no |
| Odor Problems | yes | no | no |
| Attracts pests | yes | yes | no |
| Technically complex | no | yes | no |
| Carcinogenic by-products | no | no | no |
| Conserves water | no | no | yes |
| Scale Up/Down Flexibility | no | no | yes |
| A Sustainable practice | no | no | yes |
| Simple to implement and maintain | no | no | yes |
| Capital Investment | high | high | low |
| Labor cost | high | high | low |
| Land use requirements (footprint) | high | high | low |
| Capital Re-investment Requirements | moderate | high | low |
| Operational Costs | high | high | low |
| Waste (Biomass) limits | no dairy, fats, meat | yes | no |
| Nutrient value end product to plants | moderate | moderate | high |

Fig. 1

| Date | | Water | 1_10 | 1_20 | 1_50 | 1_100 |
|---|---|---|---|---|---|---|
| 12.21.2011 | Day -14 soil and pot preparation 100 mL water added to all pots Day 5 (cm) | 4.5 | 8 | 8 | 8.5 | 7.5 |
| | Av | 4.5 | 8 | 8 | 8.5 | 7.5 |
| | stdv | | | | | |
| 12.22.2011 | Day 6 (cm) | 10.8 | 7.9 | 10.8 | 11.2 | 11.7 |
| | | 8.4 | 11 | 11.3 | 12 | 12.8 |
| | 25 mL water/tea added to each pot | 11.5 | 9.5 | 11.4 | 12 | 11.3 |
| | | 11.5 | 11.9 | 12.6 | 9.8 | 10.8 |
| | | 10.6 | 12.4 | 9.9 | 10.5 | 10.8 |
| | | 13.5 | 11.5 | 11.9 | 12.2 | 12 |
| | | 12.9 | 14.3 | 11.8 | 11.3 | 12.2 |
| | | 8.9 | 11.6 | 12.2 | 12.9 | 9.2 |
| | | 9.5 | 12.6 | 11 | 13.4 | 11.5 |
| | | | 11.9 | 11 | | |
| | Av | 10.8 | 11.5 | 11.4 | 11.7 | 11.4 |
| | stdv | 1.7 | 1.7 | 0.8 | 1.1 | 1.0 |
| 12.24.2011 | Day8 (cm) | 17 | 15.8 | 14.3 | 18.5 | 16.8 |
| | | 17 | 17.4 | 15.3 | 17.3 | 18 |
| | 25 mL water/tea added to each pot | 17.4 | 16.2 | 17.2 | 18.2 | 16.2 |
| | | 18 | 13.2 | 17 | 17.8 | 17 |
| | | 15.7 | 18 | 17.8 | 18 | 17.4 |
| | | 16.8 | 16.5 | 16.2 | 16.8 | 16 |
| | | | | | 16.8 | 14.8 |
| | Av | 17.0 | 16.2 | 16.3 | 17.6 | 16.6 |
| | stdv | 0.8 | 1.7 | 1.3 | 0.7 | 1.0 |
| 12.26.2011 | Day10 (cm) | 17.8 | 19.4 | 19.4 | 22.2 | 17.8 |
| | | 20.2 | 18.7 | 20.4 | 22.8 | 16.4 |
| | 25 mL water/tea added to each pot | 19.7 | 23.6 | 21.5 | 20.4 | 17.4 |
| | | 21.9 | 18 | 21 | 21.9 | 17.8 |
| | | 21.3 | 19.5 | 18.1 | 22.1 | 19.7 |
| | | 16.6 | 17.8 | 19.4 | 18.8 | |
| | Av | 19.6 | 19.5 | 20.0 | 21.4 | 17.8 |
| | stdv | 2.0 | 2.1 | 1.2 | 1.5 | 1.2 |
| 12.27.2011 | 100 mL water added to all pots | | | | | |
| 12.28.2011 | Day12 (cm) | 20.4 | 22 | 18.5 | 20.3 | 17.8 |
| | | 21.4 | 23.5 | 19.6 | 22 | 20.8 |
| | | 18 | 18 | 20.4 | 20.8 | 17.4 |
| | | 21.2 | 21 | 17.6 | 21 | 28.6 |
| | | 20 | 22 | 20.8 | 22.2 | 19 |
| | | 21.6 | 19.8 | 24 | 18 | 17.5 |
| | Av | 20.4 | 21.1 | 20.2 | 20.7 | 20.2 |
| | stdv | 1.3 | 1.9 | 2.2 | 1.5 | 4.3 |
| 01.02.2011 | Day 15 - Harvest and inspect root structure | | | | | |

Fig. 4

| Bokashi Tea Dilution Table (v/v) - Grass Height (cm) | | | | | |
|---|---|---|---|---|---|
| Days | Water | 1_10 | 1_20 | 1_50 | 1_100 |
| 5 | 7.5 | 8 | 8 | 8.5 | 7.5 |
| 6 | 10.8 | 11.5 | 11.4 | 11.7 | 11.4 |
| 8 | 17.0 | 16.2 | 16.3 | 17.6 | 16.6 |
| 10 | 19.6 | 19.5 | 20.0 | 21.4 | 17.8 |
| 12 | 20.4 | 21.1 | 20.2 | 20.7 | 20.2 |
| 15 | Harvest and Inspect root structure | | | | |

Fig. 6A

| Weight Measures | Hours | Soil (lbs) | Bokashi Treated Soil (lbs) |
|---|---|---|---|
| 08032011_1100 | 1100 | 16 | 16 |
| 08032011_1215 | 1215 | 19 | 19 |
| 08032011_1700 | 1700 | 18 | 18.5 |
| 08042011_2000 | 4500 | 17 | 17.5 |
| 08052011_0800 | 5700 | 17.5 | 17.5 |
| 08052011_1400 | 6300 | 17.5 | 17.5 |
| 08052011_1900 | 7400 | 17 | 17 |
| 08062011_0800 | 8700 | 17 | 17.5 |
| 08062011_1300 | 9300 | 17 | 17 |
| 08062011_1730 | 9730 | 16.5 | 17 |
| 08072011_0800 | 10960 | 16.5 | 17 |
| 08072011_1830 | 12190 | 16.5 | 16.5 |
| 08082011_0800 | 13420 | 16 | 16.5 |
| 08082011_1800 | 14620 | 16.5 | 17 |
| 08092011_0800 | 16020 | 16 | 16.5 |
| 08092011_1200 | 16420 | 15.5 | 16.5 |
| 08102011_1200 | 17620 | 14.5 | 16 |
| 08132011_1800 | 24820 | 14 | 14 |
| 08152011_1800 | 36820 | 14 | 14 |
| Moisture 8162011 meter measure | | 2.5 | 5.5 |
| Moisture 8182011 | | | |
| Pre dry weight grams | | 500 | 500 |
| Dry #1 | | 400 | 340 |
| Dry #2 | | 400 | 340 |
| Dry #3 | | 400 | 340 |
| Percent by weight Water | | 20 | 32 |
| AgrowPulp 7 pounds in 4 sq ft by 6 inches | | | |

METHOD OF PROCESSING ORGANIC WASTE

FIELD OF THE INVENTION

The present invention relates generally to a method of processing organic waste and, more particularly to processing organic waste rapidly with containment to form soil amending products using acidic anaerobic fermentation and dewatering.

BACKGROUND OF THE INVENTION

Organic waste is efficiently and effectively transformed into useful products for soil restoration. The process involves fermenting waste in a microaerophilic environment with soil microbes. Bio-Pulp obtained is then processed to separate liquid solutes from non-solubles. Processing is contained as waste is transformed minimizing or eliminating permitting requirements. The bio-cake and tea end products are packaged, stored, and used to improve soil quality. Rapidly processing organic waste into a product for soil requires a stepwise process and can be done with very high throughput and efficiency. Containment minimizes permitting requirements and avoids ground water and soil contamination.

Recycling of organic waste is an important and essential strategy that all municipalities and districts will increasingly mandate. Generally speaking it is advocated to divert waste from the landfill. Secondary considerations have to do with attempts to recover value from waste that would have otherwise been buried.

There are two commonly advocated technologies used to recycle organic waste involving either composting or methane generation by means of anaerobic digesters. Anaerobic digesters are exceptionally expensive and complex and they are unproven in large scale operations. Composting is also costly and slow and both approaches are seldom welcomed by communities because of the noxious odors, concerns about safety, and scale up costs and long term sustainability.

There is an alternative technology that involves acidic anaerobic (Bokashi) fermenting well known and practiced in many parts of the world that is efficient, rapid, non-polluting, and very inexpensive. The present invention exploits these principles to provide solutions to long sought needs in the field of the invention.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method of rapidly converting organic waste into products for treating and improving soil is disclosed. Wheat bran culture mix is used to inoculate organic waste and produce an inoculated waste material, where the wheat bran culture mix includes soil derived microbes. The inoculated waste material is shredded to produce shredded inoculated waste material which is fermented the shredded inoculated waste material for at least 7 days. Contents from the fermenter are then transferred into a dewatering device to produce dewatered contents which are then separated into soluble and suspended products.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 1 charts comparative attributes for recycling organic waste.

FIG. 4 shows a table of measured leaf length from an example experiment.

FIG. 6A and FIG. 6B show data from an example experiment relating to moisture content measurements.

DESCRIPTION OF THE PREFERRED EMBODIMENT

Figure 2:
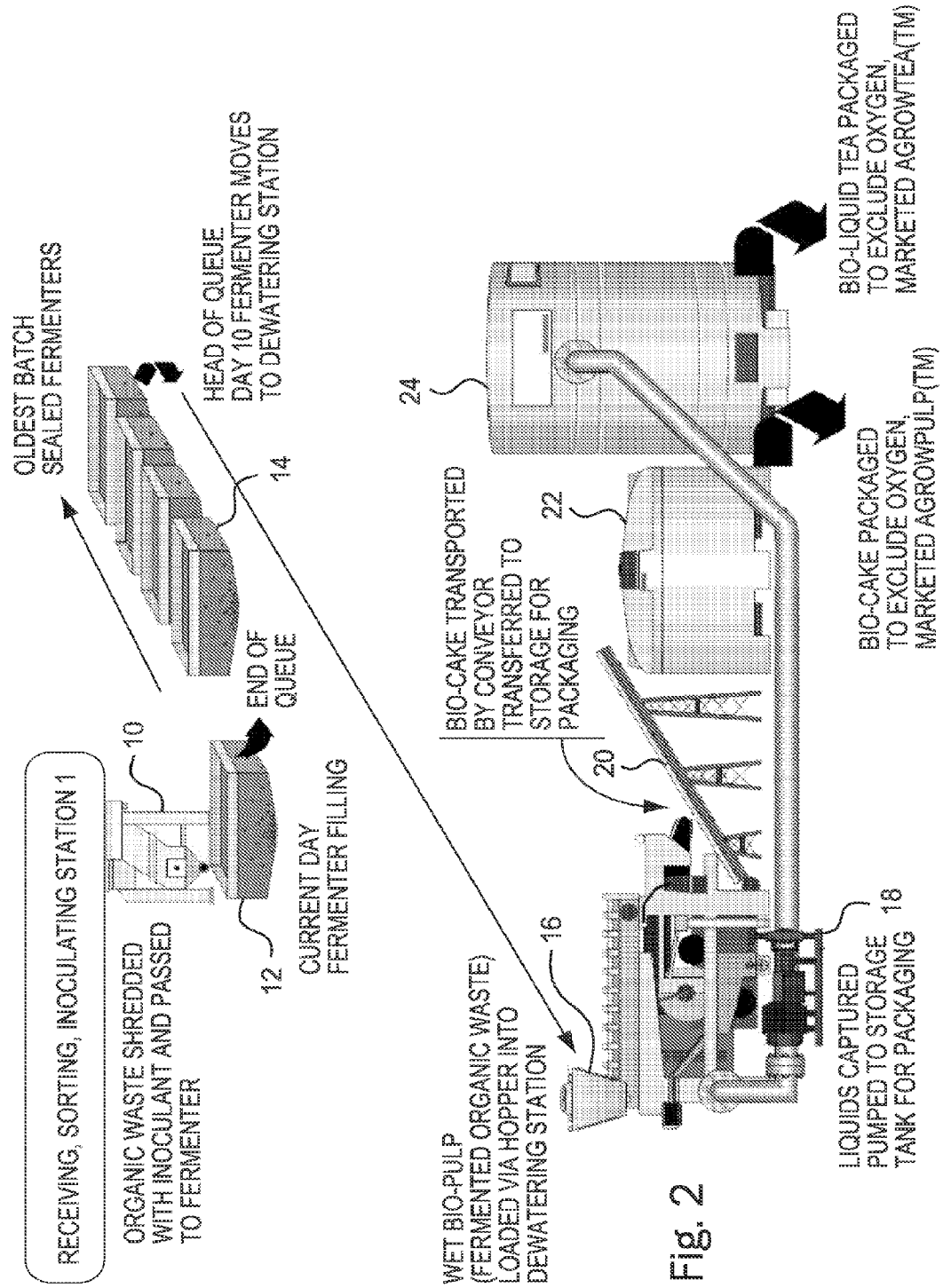
FIG. 2 shows an example of a system for processing organic waste in a continuous flow operation with containment.

The following disclosure describes several embodiments and systems for imaging an object of interest. Several features of methods and systems in accordance with example embodiments of the invention are set forth and described in the figures. It will be appreciated that methods and systems in accordance with other example embodiments of the invention can include additional procedures or features different than those shown in figures.

Example embodiments are described herein with respect to biological cells. However, it will be understood that these examples are for the purpose of illustrating the principles of the invention, and that the invention is not so limited. Additionally, methods and systems in accordance with several example embodiments of the invention may not include all of the features shown in these figures. Throughout the figures, like reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Generally as used herein the following terms have the following meanings when used within the context of optical microscopy processes: "Bokashi fermentation" means the process of pickling organic waste material.

It is done in a specialized container by excluding oxygen with microbes that are added to the food scraps in the container.

"Bokashi culture mix" means a mixture comprised of wheat bran, molasses and microorganisms and most preferably with wheat bran alone.

"Microbes" as used herein generally refer to microscopic living cellular organisms. Microbes used in one example of the Bokashi culture mix include at least three (3) different groups—Lactobacilli, Fungi/yeast, and phototropic bacilli. This combination has been proven to rapidly degrade (ferment) organic waste while suppressing the growth of other potentially dangerous organisms, but as the inventor has discovered, the wheat bran untreated and used as obtained after harvesting is satisfactory and a preferred use (see description below).

A new and novel process is disclosed here whereby organic waste is rapidly transformed into a valued soil amending material. In overview, both the liquid and solid bio-cake components are useful in this application. Both products when used in the field reduce or eliminate the need for fertilizer applications and are preferred over fertilizer because they nurture soil microbes in diversity and numbers in addition to increasing organic content of the soil. The nutrients obtained in the process are more avidly retained in the soil in this process relative to oxidized nutrients obtained by composting. The amount of liquid or solid cake applied to the soil can vary greatly and soil tests may be used to determine optimal applications for certain plants or crops.

Most importantly, it is apparent that prior teachings of how to produce a bokashi culture mix with wheat bran, molasses and specialized microbes are, in our view, misleading and incorrect.

The inventor teaches that only the wheat bran alone is required to accomplish the satisfactory fermentation of organic waste and adding molasses and other microbes to the wheat bran makes it more expensive to produce an ideal culture mix and a culture mix produced in the manner described by others who bokashi ferment by adding molasses and microbes produce a mix with a shorter shelf life than the untreated wheat bran.

The inventor teaches that virtually any field harvested grain or rice grain crop is sufficiently contaminated with fungal and other microbial spores perfectly able to rapidly and efficiently ferment organic waste in an acidic anaerobic process with no other additives or treatments. This discovery makes it practical to produce culture mix for fermenting at a level needed for industrial processing.

As described in more detail below with respect to the figures and claims, the presently disclosed process converts organic waste to a highly valued product for soil management. No other technology currently accomplishes this task so rapidly with so little effort and little cost. No turning, aerating, or additives other than the initial microbial inoculants is needed. Potential for ground water contamination is eliminated because everything is contained in the processing scheme. All of the material processed including both the liquid and solid components at the end of the process are used and valued. They replace the need to use commercial fertilizers when properly applied to soil. Carbon is sequestered and greenhouse gas reduction is immediately experienced unlike any of the other alternatives. The current invention process has the smallest foot print of any known waste processing scheme including composting and anaerobic digestion. It can be run very efficiently scaling up or down with minimal capital investment and therefore does not require a fixed contract for feedstock to operate profitably. Approximately 1000 tons of waste can be processed every month in a total space of about 25,000 square feet on a cement floor with no waste material ever contacting the floor or entering into the water table.

Other existing systems and schemes for processing organic waste consume a lot of energy. They require a lot of labor. They result in an end product with common findings of less than 50% of the nutrients relative to this inventor's system process. The other approaches require complex monitoring. They do not so efficiently process meat and dairy products. Capital expenditures are far higher than the current inventors approach to processing organic waste. They waste water and produce greenhouse gases which the inventor's process avoids. Other schemes and processes support potentially harmful pathogen growth that can infect humans. Common pathogens are $E.\ coli$, fecal $coli$ forms and salmonella. Those organisms are destroyed in the inventor's process. Other systems require time consuming and expensive permitting, containment ponds and a lot of land to process and they produce foul odors and attract pests and rodents. The inventor's system gets rid of odors and requires no complex permitting or confinement structures.

Current methods of handling organic waste are limited with few alternatives choices. Composting is tedious, expensive, and time consuming. End product has destroyed most of the microbes and much nutrient is lost by oxidation. Composting requires added carbon products and water and must be maintained, turned, and constantly monitored for success. It is slow taking months to reach an end point. The final product is used to amend soil but does little to support soil microbes. Carbon dioxide and other greenhouse gases are generated in the process contributing to global warming. Foul odors are common and vermin are a nuisance.

Anaerobic digestion with methane production is very expensive, complex and unproven in large scale operations. Maintaining a functional unit is expensive. Labor is expensive. The digestate must be treated to remove potential pathogens. Water is heavily contaminated and requires further treatment. Foul odors are common.

Acidic anaerobic fermenting (AAF) and pulp processing is rapid reaching end points in digestion 10 times faster than composting. It takes about 10 days and can be done throughout the year. End products provide needed nutrients for soil management that are not so easily leached from soil. Nutrients in the starting feedstock are retained in the process and both the tea and pulp when mixed with soil nurture soil microbes. Odors are eliminated. Vermin are not attracted to the site. AAF is labor saving, does not require input energy in processing, requires little attention in processing and results in a pulp end product that can then be quickly processed to produce soluble and insoluble matter used in amending soils. Odors are not a problem. Vermin do not come to feed at the site. All material is totally contained with no chance to contaminate the working site and surrounding ground water.

Organic waste is shredded and inoculated in one step and then sealed in a fermenter. One step gets it started.

AAF involves a rapid metabolic breakdown and pickling of waste material by microbes. The pickling process takes typically 7-10 days. No heat is generated. No vapors or gases escape into the atmosphere. No other materials are needed to efficiently make the process work. No turning machinery is needed to degrade waste. Enzymes produced by the microbes open and lyse cells resulting in much liquid rich in nutrients and microbes that can then be harvested. Because it is done in a closed container and because it is acidic and does not produce carbon dioxide, the carbon content and nutrients remain intact and no methane is generated. Separating the solids from the liquids allows the operator to then package each as separate products that can then be applied to soil for restoring rich soil nutrients and microbes. The microaerophilic fungi present in the inoculants, lack of oxygen, and acidity each contribute to the killing of fecal coli forms pathogens and salmonella, the known dangerous pathogens for humans that frequently colonize material in AD and composting operations.

Referring now to FIG. 1, the chart provides at a glance comparative attributes for the 3 methods used to handle and recycle organic waste. The three methods include standard composting, anaerobic digestion and a new and novel bokashi fermentation method as disclosed here for the first time. Note the advantages of less time and lower costs provided by the bokashi fermentation method.

Referring now to FIG. 2, there shown is an example of a bokashi fermentation system used in carrying out waste processing. Organic waste enters station 1 where it is sorted and inoculated with a wheat bran culture mix. Organic waste with inoculant begins a continuous flow process, passing first through a shredder 10 directly into a fermenter 12 which is then sealed. The sealed fermenter 12 is advanced to the end of a queue of fermenters 14 that have preceded this filling. Sealed fermenters are advanced in the order of filling. The fermenter at the head of the queue at 10 days is moved to a dewatering station 16. Fermenting is then complete.

The bio-pulp (fermented organic waste) is transferred from the fermenter 12 to the dewatering station 16. Here, bio-pulp liquids are separated from bio-pulp suspended solids. The suspended solids form a bio-cake. The bio-cake is transported by conveyer 20 to a holding tank 22. Bio-cake is then packaged to exclude oxygen and marketed as a soil amending agent.

Liquids released in the dewatering step are collected and pumped to a holding tank 24. That liquid tea is then packaged to exclude oxygen and marketed as a soil amending agent. In this operation no organic waste ever comes in contact with the ground or soil. The operation is continuous. Organic waste is rapidly converted to end product by fermenting. This operation can be done throughout the year continuously and weather has no bearing on its operation. Product may be used in the local region or shipped to any other site for sale and application.

Because the organic waste is contained during its transformation with no ground or soil contact, and is in the end free of pathogens, and the potential for ground water contamination is never allowed, the savings in permitting expense, operational expense, and containment structure cost are large.

End product bio-cake and tea are marketable products that may be used in agricultural practice, sold to nurseries, or used in residential settings to improve soil and plant performance.

Figure 3:
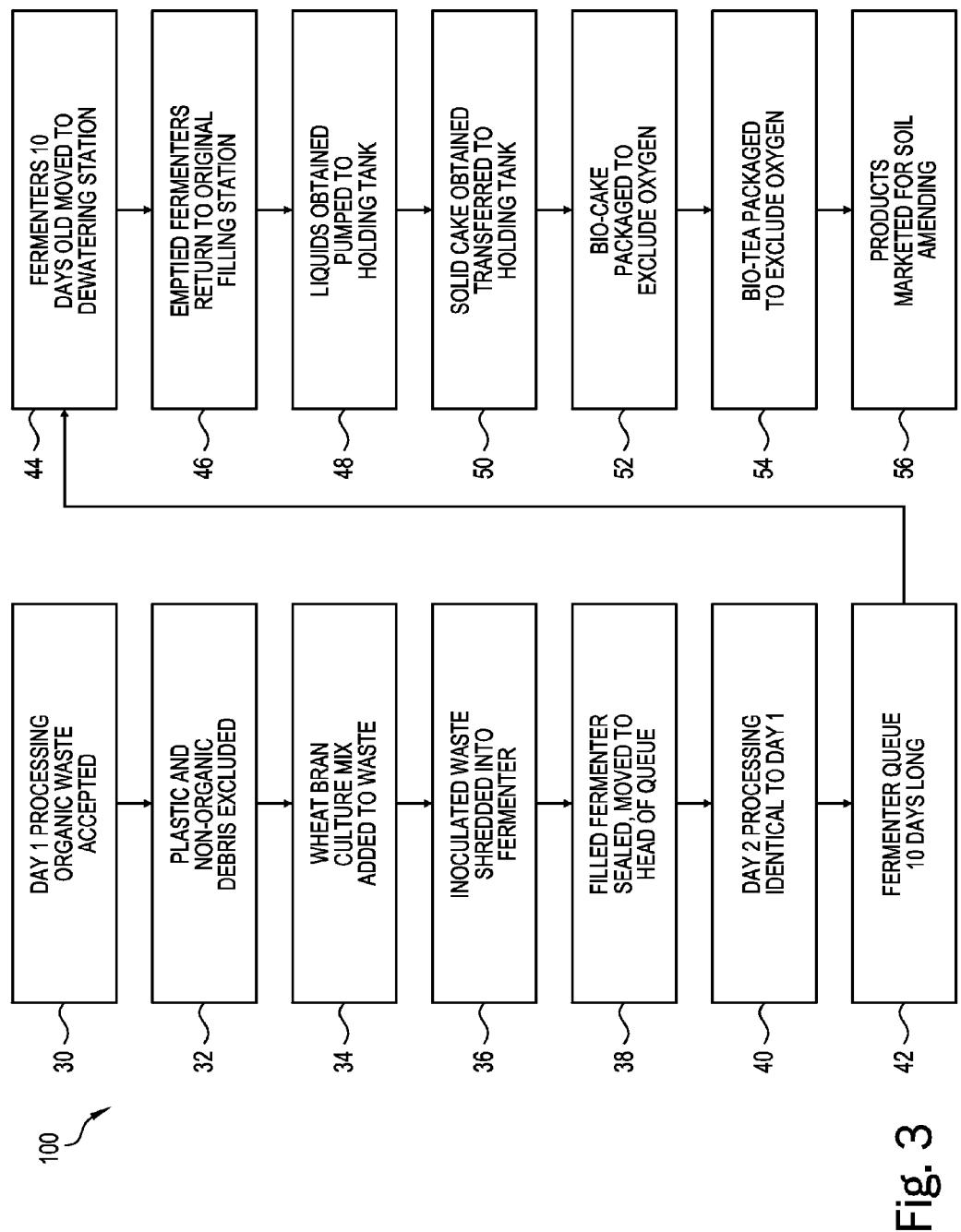
FIG. 3 shows an example of a flow sequence for continuous process conversion of organic waste to product cake and tea product lines.

Referring now to FIG. 3 a process flow of one embodiment for processing organic waste is schematically shown. The process flow shown is a step by step sequence for operations showing how fermenters fill, age, and then empty to then return to the filling station and the end of the queue with the next filling. With this cycle, all material is contained, minimal capital expense is incurred in the operation, and the amount of space needed to process even large volumes of waste is minimized.

It should also be noted that with this organization and containment, the operations may be scaled up or down easily with minimal expense by adding to or removing fermenters in the queue. The dependence on a fixed rate of waste processing to cover capital expenditures in operating the plant is eliminated.

In other competing operations, for example in composting operations or anaerobic digesting methane generating operations, the loss of feedstock can have a devastating impact on the financial success of the operation because those systems are designed for assured volumes of waste processing in order to sustain a profit.

Capital expenditures for infrastructure and equipment are large and operators can't recover their loss when assured feedstock is then lost to a competitor or just taken away. AD operators and composters can't easily expand to meet higher demands without expensive redesigning of the plant and they do not tolerate loss in feedstock without a negative impact on profitability in processing.

With the current utility invention, the only adjustments needed with changes in feedstock volume involves expanding or contracting fermenting units which are inexpensive. With a large expansion in feedstock volume one might need to add an additional dewatering unit. Dewatering units are inexpensive to install and they have a small footprint.

Still referring now to FIG. 3, a process flow of one embodiment for processing organic waste is schematically shown. A process 100 comprised of the following actions or steps. On day 1 of processing organic waste is accepted 30 including collected food scraps, and other organic waste materials to be processed in a bin or container. All dairy, meat, vegetable matter and fruits may be combined in any combination and do not need to be separated in the process. No extra carbon material or water is needed.

Plastic and non-organic debris is excluded 32 by removing non organic materials including plastics and metals of any kind before beginning the process. Compostable plastic forks, spoons, cups, or bowls are also excluded as they contain polymers that are plastic. The resultant waste is moved to the next process step.

Wheat bran culture mix is added to inoculate the waste 34. The inoculated waste material is processed with soil derived microbes provided with the wheat bran substrate. This is typically done in a single step so that shredded material with microbe inoculants is directed to filling the fermenting container as waste is being run through the shredder. Inoculating the organic waste with wheat bran culture mix is the important first step. Other culture media with soil microbes may also be used to advantage. For example rice bran or grains in general taken from the soil may be included in the culture mix.

An important discovery disclosed herein is the use of grain brans, in one preferred practice using wheat bran. Wheat bran is naturally heavily contaminated with a variety of naturally occurring soil spores, including various fungal and microbial species. No further modifications are needed and the wheat bran can be used directly to inoculate waste material for fermenting. This discovery means that no special treatments of bran are needed in preparing the culture mix used to ferment waste material. The product is more stable and less costly to produce when used in this form and rapidly under fermenting conditions converts waste to end product.

Further, there is no need to procure "EM" (effective microorganisms) commercially so frequently recommended by previous bokashi fermenters. Eliminating this requirement for the industrial scale operation results in very substantial savings in consumable inoculants and makes it easy to procure culture mix in sufficient quantity to meet the large industrial demands for inoculants. It also reduces the cost for the inoculants to the price of raw bran materials.

It is important to substantially exclude oxygen during the fermenting step and to collect liquid and solid bio-cake for packaging with the least amount of exposure to oxygen. Packaging of the product should occur on the same day as it is dewatered for best results. Packaging end product should exclude oxygen. Product may be stored in a cooler or refrigerated area to minimize degrading of nutrients and growth of aerobic organisms. End product is stabilized when packaged to substantially exclude oxygen.

Although it is important to inoculate the organic material after non-organic material has been removed, it is possible to accomplish the same end point by not removing the non-organic materials in the fermenting first step. Non-organic materials will not be processed or broken down in fermenting and may damage dewatering equipment. The preferred method is to remove non-organic material if it is present in advance of the dewatering step.

The inoculated organic waste is then shredded with a shredder or chipper 38. The shredded inoculated waste is allowed to fill a fermenter directly. The fermenter is labeled or identified by date of filling to track the number of days fermentation is to be processed. The fermenter is sealed at the end of the filling or at the end of the day it is loaded. Shredding is an important step that results in a more efficient fast decomposing of waste material that is inoculated but is not required. It also makes it easy to evenly inoculate the waste with wheat bran culture mix since the mixing of powder culture mix with waste is efficiently accomplished in the shredding step. The microbes can move with fluids throughout the fermenting cycle so uniform inoculating or shredding is not an absolute requirement in the process.

The fermenting device may advantageously comprise a contained enclosure made substantially of either plastic or steel coated with a plastic liner of polypropylene, polyethylene or equivalents that can be sealed after filling to exclude oxygen. In one example embodiment a plurality of fermenters may be used where each fermenter has an identification number that is used for tracking processes. The date the fermenter is filled may be recorded. Emptied fermenters are returned to filling positions under the shredding and inoculating station.

Day 2 processing up to Day 10 follows the procedure detailed above 40. That is it is substantially identical to Day 1 processing steps. Fermenters are allowed to age to 7 to 10 days before they are opened and emptied.

After 7-10 days for any fermenter in process, the contents are transferred mechanically from the fermenter into a device dewatering 44 so that the soluble and suspended products at the end of fermentation can be separated. The pulp fermented product is allowed to feed through a hopper into a screw press or equivalent dewatering device. A vapor barrier is normally in place. The screw press separates liquid from solids. The liquid is collected and sealed in containers to exclude oxygen. These containers should be plastic or glass because of the acidity of the liquid. The bio-cake obtained is immediately transported to bags or plastic drums that are sealed to exclude oxygen.

Emptied fermenters are returned to a filling station 46. The empty fermenter can be put back through the same cycle again and again. There is no need to wash or clean the fermenter in the cycle process.

Culture studies on 3M Petri film have demonstrated coliforms do not survive this process. The fermenting process disclosed in this patent yields a processed waste for recycling free of coliforms. This is accomplished metabolically at or near room temperature and is an advantage over composting or anaerobic digester methods of waste processing that do not so readily eliminate these human pathogens.

This process continues indefinitely day after day with empty fermenters cycling back to receive freshly inoculated and shredded organic waste. Fermenters process waste in a room temperature environment at 25+/−10 C.

The preferred temperature for fermenting is at or near room temperature. However the fermenting will proceed over a wide range of temperatures and it is not necessary to monitor and or control daily temperatures. Because there is no heat generated in fermenting and no loss of water due to evaporation, no additional water is needed in this process. This results in additional savings in consumables.

Excluding oxygen is an important part of the fermenting process but absolute exclusion is not a requirement. Typically, the oxygen tension will be in the neighborhood of 1% or less. Even higher surface area oxygen tensions may not inhibit processing deeper in the wet pulp material where oxygen is naturally excluded. Sealing the container and excluding oxygen is a savings in time and energy as no further tending is needed until the waste is transformed to fermented bio-pulp. Mixing, turning, watering, and aerating steps are eliminated savings energy and money in processing waste.

Fermenting is generally complete in the range of 7 to 10 days and the pH of the pulp material will be typically between 3.5 and 5.5. A steady non declining pH near 3.5 or 4.0 is a good sign that the end point of fermenting has been reached and is a common finding in industrial scale processing. It is possible to exclude oxygen by blanketing the processing waste with an inert gas or carbon dioxide gas but closing the fermenter mechanically is preferred.

Separation of soluble and insoluble products is typically accomplished with a screw press which produces a bio-cake (powder) of insoluble processed material and liquid (tea) of water soluble material obtained by fermenting. The liquid component, known as "tea," is directed to containers or holding tanks 48 that are then sealed so oxygen is excluded. The solid bio-cake obtained after dewatering may be transferred to a holding tank 50 or immediately bagged and sealed to exclude oxygen 52. The liquid and solid components are marketed as soil amendments 54, 56. They may be added in combination or separately to the soil.

Dewatering the end product may be accomplished in many ways. Dewatering can be done by using centrifugation, pressing, filtering, or screen pressing. The bio-cake produced will typically end up dewatered to 10 to 20% of the mass of the wet pulp taken from the fermenter. If processing is done in the field, the wet pulp at the end of the fermentation may be directly added to the soil without dewatering. Dewatering results in a more stable product that can be stored and shipped and then applied to soil to feed the soil microbial flora.

The liquid tea and the solid pulp obtained after fermentation and dewatering are valued products useful in treating soils. Because the mass of waste material fermented is retained in either liquid or solid forms after being metabolized, a higher percentage of carbon and other nutrients are returned to soil when the tea and solids are applied to soil. This results in a higher percentage of carbon sequestration and a richer nutrient load of metabolites going directly into the soil. Soil microbes will metabolize those nutrients expanding their populations in number and diversity. This feeding of the soil microbial flora is an important use for end fermented waste materials resulting in richer healthier soils that can then support plants and products grown in the soil.

Adding fermented waste either as the wet bio-pulp or as the separated tea and pulp results in soil with a higher organic content. The soil treated in this matter will retain and hold water as we have demonstrated in experiments making such soil more resistant to draught.

Experiments have demonstrated that plants treated with either tea or pulp or the combined wet pulp show more blooms and foliage relative to plants in identical untreated soil. In one preferred mode of operation, organic waste material is collected and immediately seeded with wheat bran culture mix. For each ton of organic waste 10 to 30 pounds of wheat bran is added by spreading the wheat bran mix evenly over the waste material.

Solid and liquid products harvested are marketed as soil amendments. The solid bio-cake can be applied to soil by tilling with an application rate of 5 to 20 pounds per square foot. The liquid product will normally be diluted 1:50 with water up to 1:1000, but ideally 1:100 v/v and then applied as would be common in watering or drip irrigation.

Robotic machines with computer interfacing may be employed to handle all operations in this process.

EXAMPLES

Example 1

AgrowTea™ Impact on Wheat Berry Grass Seedlings

A pilot study was done to assess the impact AgrowTea watering has on Wheat berry grass seedlings. Wheat berry grass seeds were placed in a container with tap water and allowed to soak overnight. Seedlings were allowed to germinate in six inch pots filled with garden soil to which water and or diluted AgrowTea was added. Leaf length was measured and followed for a period of approximately 2 weeks at which time no further growth was observed. Plants were watered with plain water or AgrowTea (see Table in FIG. 4).

Full grown Wheat berry grass bunches were then carefully removed from their pots. Root structure was examined after carefully removing residual soil with cold water washing. It was apparent that even small amounts of AgrowTea added to the soil resulted in a high density root structure.

Numerous lateral shoots were observed directly beneath the soil forming a crown and root matrix most apparent in a stereoscopic microscopic examination and it appears related to the dilution ratio of tea to water. Although the crown and matrix root structure was evident in all pots, it was most evident at a 1:50 (tea to water) dilution ratio and least evident when only water was used.

AgrowTea™ is a liquid extract obtained by fermenting organic waste that is rich in microbes, trace minerals, nutrients and fermented metabolized fibrous debris free of pathogens used in the field to restore microbial flora and organic content. It is the end product of acidic anaerobic (Bokashi) fermenting after the Bokashi bio-pulp (Agrow-Pulp™) separation is done.

Study Purpose:

In this study the objective was to track with measurements leaf length in real time in a model closely simulating field conditions. We wanted to observe the impact of watering with water or diluted AgrowTea at ratios of 1/10, 1/20, 1/50 or 1/100 to see if a concentration effect was measureable in either leaf or root structure.

We obtained measurements on a daily or every other day basis over a 2 week period with 30 seeds per pot and 3 pots for each dilution ratio including a set of 3 pots (90 seedlings) for water only observations.

Experimental Design:

Ordinary garden soil was filtered through ¼ inch wire mesh to obtain a uniform size potting soil mix. Six inch pots were filled ¾ full with this soil and a single application of either tea or water (see Table below) was added 14 days before seeds were planted in the pots.

Wheat berry grass seeds were obtained from Living Whole Foods, Inc Springfield, Utah and soaked overnight in tap water. Thirty seeds were then placed in each pot, 3 pots per dilution ratio and set aside to sprout. The soaked seeds were covered with approximately ½ inch of soil that was firmly tamped down to cover the soaked seeds.

The pots were then placed in grow trays under grow lights (100 watt) and subjected to approximately 12 hours of light each day at room temperature. Each day measurements were obtained, one of 3 pots in a particular group was taken at random and 6-10 leaf lengths were measured to the nearest millimeter from the soil surface to the leaf tip. An average length for that day measurement was then calculated.

At the end of the experiment, Wheat berry grass bunches were removed from pots and placed in cold water. Most of the soil was in this way easily removed without disrupting or damaging root structure. Roots were also washed gently with a stream of cold water. They were then placed on a cardboard matt. Photographs were taken to document root density. A stereoscopic microscope was then used to inspect root structure for each dilution level studied.

Data Obtained:

The germination and sprout percentages were high with nearly 100 of the seeds resulting in a sprout for all pots in the study. The first measurements started 5 days after the seeds were planted. All the pots in the study were positioned in the grow trays beneath grow lights. There were 4 pots for the dilution 1/50 tea dilution and an extra 1 gallon container at a 1/20 dilution ratio.

Pots were placed in random positions and rotated daily to assure all pots obtained the same level of lighting over the period of testing. Watering volumes and times are as indicated in FIG. 4. Pots were labeled 0/0 (water) or 1/10, 1/20, 1/50 or 1/100 for tea dilutions (volume tea to volume of water). Fourteen days before seeds were planted the soils were moistened with 100 mL of water or tea at the dilution level indicated by label.

During this pilot, pots were again watered each with 25 mL of water or tea dilution levels as indicated by label on Day 6 and Day 8.

On day 11 all pots were watered with 100 mL of water.

On day 15 the study was complete and root structure was examined as described (above).

Control Soil:

Water only treated soils were used as the control against which all other dilutions in the series of tea to water dilutions were measured.

Findings:

Wheat berry grass grows quickly reaching its full height in slightly less than 2 weeks. We have plotted the leaf length average for plants treated differently as a function of the dilution tea level applied.

With the exception of a 100 mL loading 14 days before seeds were planted and the 2, 25 mL applications of diluted tea no other soil treatments were applied in this study that could alter soil or plant response.

Figure 5:
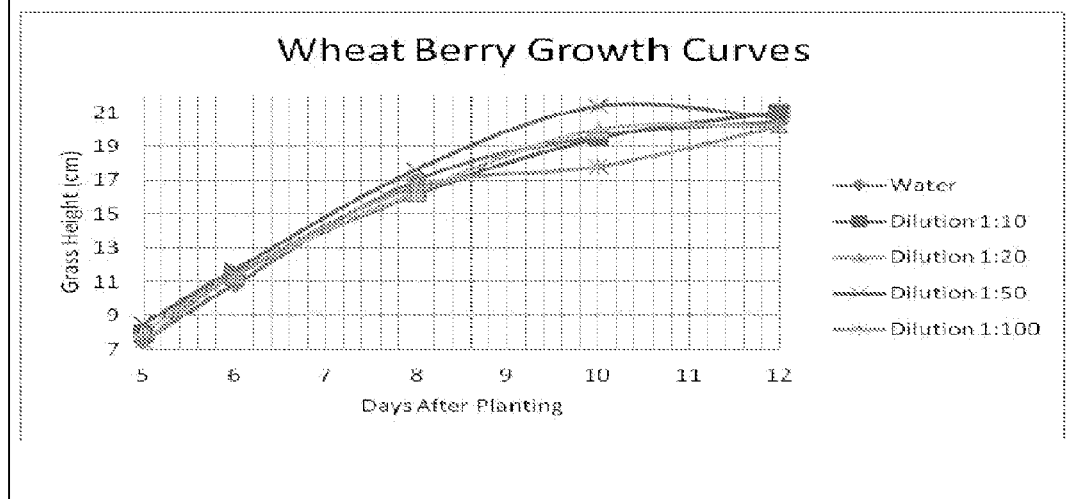
FIG. 5 shows a table and graph of wheat berry growth curves from an example experiment.

In the short 12 day growth interval for Wheat berry grass we could not establish statistically significant leaf length differences in growth curves relating to dilution levels although the 1:50 dilution trends consistently higher Table 2 as shown in FIG. 5.

However, examination of root structure revealed a clear difference in beneath the soil root structure as a function of tea dilutions. Roots extended downward from the crown with filamentous branching. There were 30 seedlings in each pot. In the pots given water in place of diluted tea there was minimal lateral cross-linking structure. Seedlings separated readily and little lateral root structure was evident.

In all AgrowTea™ treated seedlings there was abundant lateral growth in root structure forming an increasing dense matrix of roots beneath the soil most evident in the 1/50 dilution ratio. At a dilution of 1/100 the matrix was less dense than at the 1/50 dilution which was more intense than either the 1/20 or 1/10 dilution.

Stereoscopic microscopic examinations revealed many more lateral cross-linking root strands forming a denser matrix beneath the soil most evident in the 1/50 tea dilution treated soil.

Conclusions:

It appears that AgrowTea treated soils have had an impact most evident on root structure for Wheat berry grass seedlings. Although there is a consistent trend indicating 1/50 dilutions favor faster growth it is statistically insignificant in the short interval followed and at the low level dilution soil treatments.

Root density does appear greater in treated seedlings. This is more intense at a 1/50 dilution and less evident at 1/10, 1/20 and 1/100 dilutions.

Example 2

Water Content and Retention

Study Purpose:

In this study the objective was to track with measurements water content and retention in real time in a model closely simulating field conditions. Soil samples were tracked without disrupting or disturbing the soil surface. Measurements were taken over a 15 day period with no added water except in the first day of the experiment.

We obtained measurements on a daily basis in a weather exposed environment in the field to determine if soil treated with AgrowPulp in a 2 week period retained any more or less water than soil identical in every respect except for the addition of AgrowPulp.

Experimental Design:

Experiments were done in the field. Two soil samples were collected from the same area and were then put into monitoring trays. The samples were left undisturbed with the exception of weight recordings. After each weight, the monitoring trays were placed back on the ground. After each weight measurement, the position of the monitoring trays was switched from control to treated space and from treated space to control to eliminate any possible difference in ground conditions. Measurements were taken on both samples over the next 15 days.

Data Obtained:

Daily weights were recorded. At the end of the experiment the moisture content was determined for both samples using a commercially available Mosser Lee Soil Master meter. Moisture content was also determined at the beginning and end of the experiment on soil samples by determining dry weight relative to weight obtained before drying.

Monitoring Tray Design:

Two white plastic trays were used to hold and monitor samples during the experiment. The monitoring trays measure 12.times.18.times.6 inches. Each tray was fitted with a water permeable bag that was open at the top that was filled with soil to near the tray brim. The membrane did not cover any part of the upper surface.

Both trays had 4, 4 inch diameter holes on the bottom so that any water trapped in the tray could easily pass through the membrane to soil beneath the trays which were placed adjacent to each other with the same weather exposure on a flat ground surface.

AgrowPulp Treated Soil:

In one plot, 7 pounds of AgrowPulp was mixed with soil to a depth of 6 inches in an area measuring 4 square feet. This represents an application rate of 1.75 pounds per square foot which is considerably below typical applications rates of 10 to 20 pounds per square foot we recommend in farming operations. After 1 week, 16 pounds of soil from the AgrowPulp treated area was put into the monitoring tray for AgrowPulp treated soil.

Control (Untreated) Soil:

The control soil specimen was collected at the same time and placed in the monitoring tray for "untreated" soil. Sixteen (16) pounds of control soil was put in the monitoring tray.

Both the control (untreated) monitoring tray and AgrowPulp treated soil monitoring trays were then placed on flat ground with the identical weather exposure. Neither tray was shaded.

Findings:

The water content of the soil sample was determined at the beginning of the experiment by measuring approximately 400 grams of soil taken from the bokashi treated soil. The soil was then heated on an electric plate to a dry constant weight. The initial water content is as indicated in the table:

| Dry Weight Determination of Moisture Content | Weight (grams) |
| --- | --- |
| Soil Sample before drying | 400 |
| Dry weight # 1 | 290 |
| Dry weight # 2 | 245 |
| Dry weight # 3 | 241 |

Calculated Moisture Content 40%

Daily Weight Measurements:

Over the next several days, each monitoring tray was measured at various times throughout the day. Each monitoring tray weighed 16 pounds on day 1 at 10 AM. They were placed on a flat surface on the ground and watered by a sprinkler for 1 hour. After 1 hour, the sprinkler was turned off and weights were obtained 15 minutes later. Both monitoring trays weighed 19 pounds.

Figure 6B:
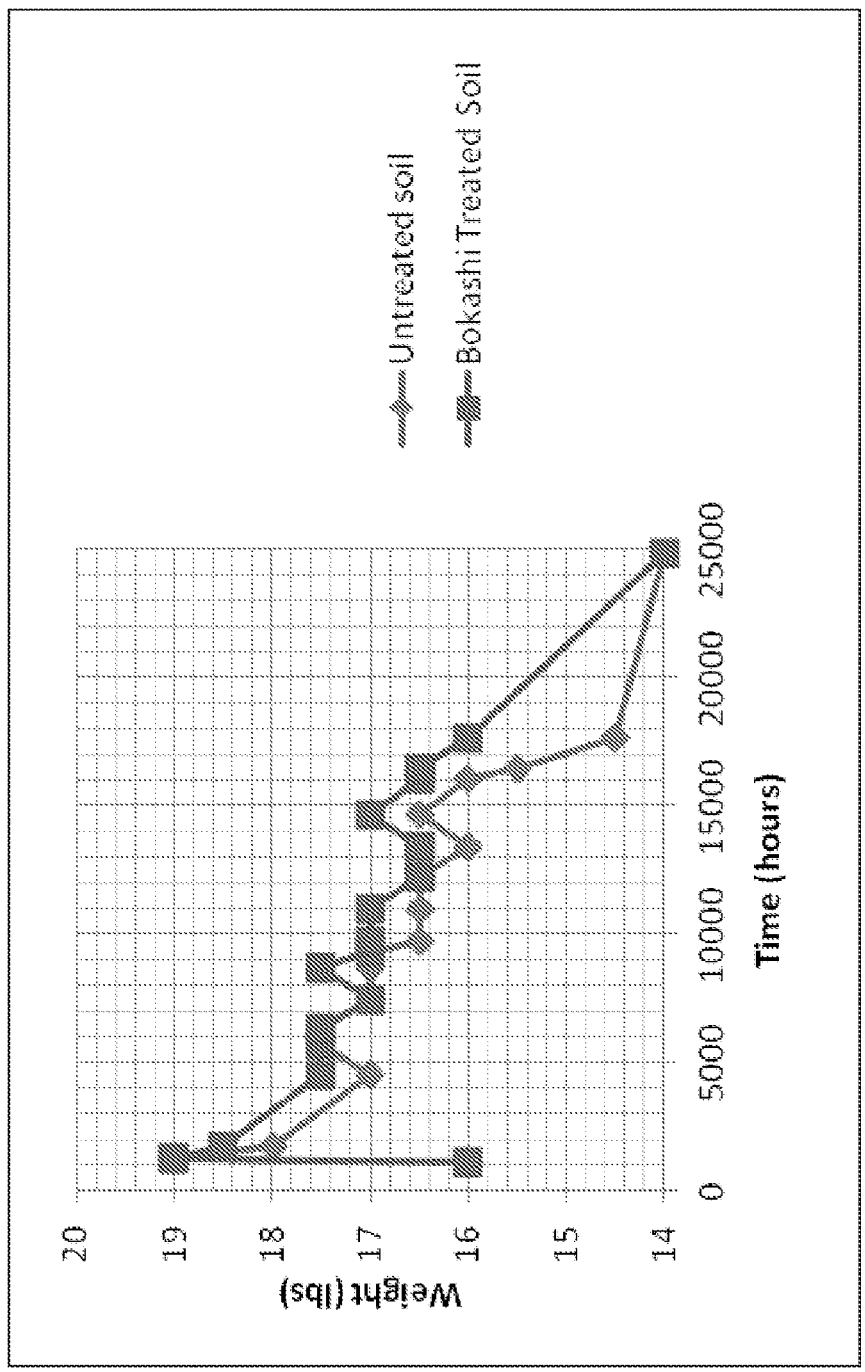

Weights at various times in the day are recorded and plotted out to 15 days for both monitoring trays. During this period no additional water was added other than what occurred naturally with a few very mild and short periods of rainfall. These results appear in FIG. 6A-6B.

In addition, meter readings and water content by dry weight determinations are provided for Day 15. At the end of the study, soil treated with AgrowPulp was substantially higher in moisture content (32% compared to 20%) relative to untreated soil. After 15 days a simple moisture content measurement reveals much more water is retained in soil treated with AgrowPulp than soil that was not treated. This was also confirmed with an independent dry weight analysis. AgrowPulp treated soil measured 32% by weight water against only 20% by weight for untreated soil.

Conclusions:

Adding AgrowPulp to soil does improve the water retaining characteristics in soil. Even with watering applications (irrigation, or by rain) the AgrowPulp appears to hold the water avidly slowing the rate of water loss. Daily weights for the monitoring trays reveal different rates of water loss. The red-line curve representing AgrowPulp treated soil is consistently above the blue-line curve for control sample. Water in the control sample depletes rapidly whilst AgrowPulp treated soil slows the rate of water loss. Retention of water in arid conditions will improve plant survival and growth and will translate into lower costs in production related to water conserving properties for the soil.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A method of rapidly converting organic waste into products for treating and improving soil comprising the acts of:
   collecting waste in a container;
   excluding non-organic debris by removing non organic materials including plastics and metals to generate an organic waste;
   introducing wheat bran culture mix consisting of wheat bran and field harvested microbes to inoculate the organic waste and produce an inoculated waste;
   shredding the inoculated waste material to produce shredded inoculated waste material;
   filling a fermenter with the shredded inoculated waste material;
   sealing the fermenter to substantially exclude oxygen during fermentation;
   fermenting the shredded inoculated waste material for at least 7 days until the fermenter reaches a non-declining pH value in the range of 3.5 to 4.0;
   separating the contents into soluble and suspended products at the end of fermentation; and
   collecting the soluble and suspended products as liquid tea and solid bio-cake respectively while limiting exposure of the collected soluble and suspended products to oxygen.

2. The method of claim 1 further comprising packaging the liquid and solid bio-cake products after dewatering.

3. The method of claim 2 wherein packaging further comprises packaging that substantially excludes oxygen.

4. The method of claim 1 wherein fermenting comprises fermenting in a fermenting device including a contained enclosure made substantially of either plastic or steel coated with a plastic liner of polypropylene, polyethylene or equivalents that can be sealed after filling to exclude oxygen.

5. The method of claim 1 where a plurality of fermenters are cycled through the acts of filling a fermenter, sealing and fermenting followed by separating the contents and collecting.

6. The method of claim 1 wherein the organic waste comprises waste selected from the group consisting of food scraps, meat, dairy and vegetable matter.

7. The method of claim 1 wherein shredding and inoculation are done simultaneously so that shredded material with microbe inoculants is directed to filling the fermenting container as waste is being run through the shredder.

8. The method of claim 1 further comprising amending soil with the liquid tea and solid bio-cake.

9. The method of claim 1 further comprising eliminating noxious foul odors associated with putrefaction.

10. The method of claim 1 wherein fermenting is limited to 10 days.

11. A bio-pulp product produced by the method of claim 1.

12. The method of claim 1 wherein all acts are completed within 10 days.

13. The method of claim 1 further comprising sequestering carbon and other nutrients into treated soil by applying the liquid tea and solid bio-cake.

14. The method of claim 1 further comprising expanding naturally occurring soil microbial flora in numbers and diversity by feeding them nutrients derived from the liquid tea and solid bio-cake.

15. The method of claim 1 further comprising returning nitrogen, phosphorous, potassium and trace minerals to soil by amending with liquid tea and solid bio-cake.

16. The method of claim 1 further comprising increasing carbon sequestration percentages by fermenting and then mixing liquid tea or solid bio-cake with the soil.

17. The method of claim 1 further comprising recycling the solid bio-cake to the soil as a bio-pulp.

18. The method of claim 1 further comprising packaging the bio-cake or liquid tea or combinations thereof into a stable marketable product in no more than 10 days.

19. The method of claim 1 further comprising eliminating coliforms and other human pathogens that can't survive in the acidic anaerobic environment.

20. A method of rapidly converting organic waste into products for treating and improving soil comprising the acts of:
   collecting waste in a container;
   excluding non-organic debris by removing non organic materials including plastics and metals to generate an organic waste;
   introducing wheat bran culture mix consisting of wheat bran and field harvested microbes to inoculate the organic waste and produce an inoculated waste;
   shredding the inoculated waste material to produce shredded inoculated waste material;
   filling a plurality of fermenters with the shredded inoculated waste material;
   sealing each of the plurality of fermenters to substantially exclude oxygen during fermentation;
   fermenting the shredded inoculated waste material for at least 7 days until each fermenter reaches a non-declining pH value in the range of 3.5 to 4.0;
   separating the contents into soluble and suspended products at the end of fermentation; and
   collecting the soluble and suspended products as liquid tea and solid bio-cake respectively while limiting exposure of the collected soluble and suspended products to oxygen.

* * * * *